US009517098B2

(12) United States Patent
Anderson (10) Patent No.: US 9,517,098 B2
(45) Date of Patent: Dec. 13, 2016

(54) BONE FUSION DEVICE

(71) Applicant: Biomet Manufacturing, LLC, Warsaw, IN (US)

(72) Inventor: David Anderson, Winona Lake, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 647 days.

(21) Appl. No.: 13/935,107

(22) Filed: Jul. 3, 2013

(65) Prior Publication Data

US 2015/0012050 A1  Jan. 8, 2015

(51) Int. Cl.
*A61B 17/88* (2006.01)
*A61B 17/72* (2006.01)
*A61B 17/68* (2006.01)

(52) U.S. Cl.
CPC ....... *A61B 17/8872* (2013.01); *A61B 17/7233* (2013.01); *A61B 17/7291* (2013.01); *A61B 17/686* (2013.01); *A61B 17/8875* (2013.01); *A61B 2090/037* (2016.02)

(58) Field of Classification Search
CPC ............. A61F 2/4225; A61F 2002/423; A61B 2090/037; A61B 17/8872
USPC ...... 623/21.15, 21.19; 606/309; 411/89, 389
See application file for complete search history.

(56) References Cited

U.S. PATENT DOCUMENTS

| | | | | |
|---|---|---|---|---|
| 3,842,824 A | * | 10/1974 | Neufeld | A61B 17/8863 606/101 |
| 4,959,065 A | * | 9/1990 | Arnett | A61B 17/8085 606/285 |
| 5,141,373 A | * | 8/1992 | Kendall | F16B 19/1063 403/408.1 |
| 5,248,231 A | * | 9/1993 | Denham | F16B 19/1054 411/38 |
| 5,409,486 A | * | 4/1995 | Reese | A61B 17/8605 411/187 |
| 5,643,321 A | * | 7/1997 | McDevitt | A61B 17/0401 606/232 |
| 5,810,530 A | * | 9/1998 | Travis | F16B 19/1054 411/34 |
| 5,814,071 A | * | 9/1998 | McDevitt | A61B 17/0401 606/144 |
| 5,989,255 A | * | 11/1999 | Pepper | A61B 17/8685 606/306 |
| 6,042,584 A | * | 3/2000 | Pierson, III | A61B 17/88 411/5 |
| 6,511,481 B2 | * | 1/2003 | von Hoffmann | A61B 17/68 606/60 |
| 6,723,099 B1 | * | 4/2004 | Goshert | A61B 17/0642 606/329 |
| 7,041,106 B1 | | 5/2006 | Carver et al. | |
| 7,074,203 B1 | * | 7/2006 | Johanson | A61F 2/0811 411/34 |

(Continued)

*Primary Examiner* — David Bates
(74) *Attorney, Agent, or Firm* — Schwegman Lundberg & Woessner, P.A.

(57) ABSTRACT

A bone fusion device includes a first anchor for insertion into a hole formed in a first phalange, and a second anchor for insertion into a hole formed in a second phalange. A rod includes a handle and a distal end, with the distal end being associated with each of the first anchor and the second anchor. The rod includes a breakaway portion between the handle and the distal end allowing the handle to be manually separated from the distal end.

19 Claims, 9 Drawing Sheets

(56) References Cited

U.S. PATENT DOCUMENTS

| | | | | |
|---|---|---|---|---|
| 7,641,677 B2* | 1/2010 | Weiner | ............... | A61B 17/685 |
| | | | | 411/389 |
| 8,529,611 B2* | 9/2013 | Champagne | ....... | A61B 17/7225 |
| | | | | 606/301 |
| 8,579,567 B2* | 11/2013 | Escarpit | ............. | F16B 19/1045 |
| | | | | 411/24 |
| 8,696,249 B2* | 4/2014 | Steyn | ................. | E21D 21/0093 |
| | | | | 405/259.1 |
| 8,834,572 B2* | 9/2014 | Averous | .................... | A61F 2/42 |
| | | | | 623/16.11 |
| 8,932,336 B2* | 1/2015 | Nardini | ............... | A61B 17/683 |
| | | | | 606/217 |
| 9,011,504 B2* | 4/2015 | Reed | ................. | A61B 17/7225 |
| | | | | 606/314 |
| 9,044,313 B2* | 6/2015 | Heaven | ................ | A61F 2/0805 |
| 9,056,014 B2* | 6/2015 | McCormick | ............ | A61F 5/019 |
| 2007/0218750 A1* | 9/2007 | Corrao | ............... | A61B 17/8605 |
| | | | | 439/404 |
| 2011/0004255 A1* | 1/2011 | Weiner | ............... | A61B 17/1682 |
| | | | | 606/301 |
| 2011/0301652 A1* | 12/2011 | Reed | ................. | A61B 17/7291 |
| | | | | 606/319 |
| 2013/0030475 A1 | 1/2013 | Weiner et al. | | |
| 2013/0131822 A1 | 5/2013 | Lewis et al. | | |
| 2013/0190831 A1* | 7/2013 | Ek | ......................... | A61F 2/4225 |
| | | | | 606/315 |
| 2013/0274814 A1* | 10/2013 | Weiner | .................. | A61B 17/68 |
| | | | | 606/301 |
| 2014/0052196 A1* | 2/2014 | McGinley | .......... | A61B 17/8605 |
| | | | | 606/319 |

\* cited by examiner

BONE FUSION DEVICE

BACKGROUND OF THE INVENTION

1. Field of the Invention

The present invention relates to bone fusion devices, and, more particularly, to bone fusion devices for fusing phalanges together.

2. Description of the Related Art

Digital deformities of the fingers and toes are some of the most common conditions encountered by orthopedists and podiatrists. Patients with digital deformities often experience significant pain from structural abnormalities. Some of these abnormalities are acquired, caused by traumatic injuries, neuromuscular pathologies, systemic diseases, or mechanical problems secondary to extrinsic pressures. The deformities are popularly known as either mallet finger, jersey finger, coach's finger, hammertoe, as well as a host of others indicative of several different pathologies.

Hammertoe deformity, the most common deformity of the lesser toes, is a flexion deformity of the proximal interphalangeal (PIP) joint of the toe, with hyperextension of the metatarsophalangeal (MTP) and distal interphalangeal (DIP) joints. Progressive PIP joint flexion deformity typically leads to compensatory hyperextension of the MTP and DIP joints. This makes the PIP joint prominent dorsally. Pain occurs due to rubbing of the prominence against the patient's shoe. The deformity is flexible at first but usually becomes fixed over time. When the deformity is flexible, various procedures can be utilized that involve manipulation of the involved tendons (such as orthotics). However, when the deformity is fixed, PIP fusion or joint replacement is often required.

In order to prevent recurrence of the deformity and ensure the success of the surgical procedure, a PIP joint arthrodesis is typically performed. The "end-to-end" or "peg-in-hole" techniques are the most commonly used procedures. The PIP joint is aligned with the rest of the toe in a corrected anatomical position and maintained in place by the use of a Kirschner wire (K-wire) of a selected diameter which is driven through the joint.

Another type of PIP joint fusion technique utilizes a fusion pin rather than a K-wire driven through the PIP joint. Referring to U.S. Pat. No. 7,041,106 (Carver et al.), which is assigned to the assignee of the present invention, an interphalangeal fusion pin may be used at a PIP joint of a human foot. The fusion pin may have an anatomically correct angle for the PIP joint (FIG. 4 of the '106 patent; e.g., 172.5°, and may be formed from a bioresorbable material.

SUMMARY OF THE INVENTION

The present invention provides a bone fusion device with anchors which are placed into respective holes formed in adjacent bones. A handle may be grasped by hand or with a tool. The handle is attached at a distal end either directly with one of the anchors, or indirectly to one or both anchors through a pin. The handle has a breakaway portion at the distal end which allows the handle to be manually separated from the attached anchor or pin.

The invention in one form is directed to a bone fusion device, including a first anchor for insertion into a hole formed in a first phalange, and a second anchor for insertion into a hole formed in a second phalange. A rod includes a handle and a distal end, with the distal end being associated with each of the first anchor and the second anchor. The rod includes a breakaway portion between the handle and the distal end allowing the handle to be manually separated from the distal end.

In one variant, the first anchor and the second anchor are discrete parts. The first anchor includes a first axial bore and the second anchor includes a second axial bore. The distal end of the rod defines a pin including a first end insertable into the first axial bore and a second end insertable into the second axial bore.

In another variant, the first anchor and the second anchor are monolithic, with the distal end of the rod being coupled with the second anchor at the breakaway portion.

The invention in another form is directed to a bone fusion device including at least one anchor for insertion into a hole formed in a bone, and a rod including a handle and a distal end. The distal end is associated with each anchor. The rod includes a breakaway portion between the handle and the distal end allowing the handle to be manually separated from the distal end.

The invention in yet another form is directed to a method of fusing adjacent bones together, including the steps of: forming a first hole in an end of a first phalange; inserting a first anchor into the first hole; providing a rod including a handle and a distal end, the distal end being associated with the first anchor; separating the rod at a breakaway portion between the handle and the distal end; forming a second hole in an end of a second phalange; and inserting a second anchor into the second hole.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplification set out herein illustrate embodiments of the invention, and such exemplifications are not to be construed as limiting the scope of the invention in any manner.

DETAILED DESCRIPTION OF THE INVENTION

Referring now to the drawings, and more particularly to FIGS. 1-4, there is shown an embodiment of an anchor 10 forming part of a bone fusion device 12 (discussed in more detail below with reference to FIGS. 7-9) of the present invention. In the illustrated embodiment, the bone fusion device is assumed to be used during a surgical procedure for the correction of a hammertoe condition. However, it is to be understood that the bone fusion device of the present invention may be used for fusing other adjacent bones together. Moreover, only a single anchor 10 is shown in FIGS. 1-4 for the purposes of illustration. However, it is to be understood that during a surgical procedure using a bone fusion device of the present invention, a second anchor will likely be used which is substantially identical to anchor 10 shown in FIGS. 1-4. Accordingly, for purposes of discussion, anchor 10 is assumed to be a first anchor used during a surgical procedure, with a substantially identical second anchor 14 (shown in FIGS. 7-9) also being used during the surgical procedure.

First anchor 10 includes a body 16 with a first axial bore 18. Body 16 includes a plurality of anti-rotation features 20 to inhibit rotational movement of first anchor 10 relative to a respective phalange when first anchor 10 is placed within a corresponding hole formed in the phalange. In the illustrated embodiment, anti-rotation features 20 are in the form of a plurality of radially movable tabs, each with an ear 22 which extends radially outward from the outer circumference of body 16 when in an at-rest position. Each ear 22 has a ramped surface 24 facing the pointed, closed end 26 which allows the ear 22 to be biased radially inwardly when first anchor 10 is inserted into a hole in a bone. In the embodiment shown in FIGS. 1-4, first anchor 10 includes four ears 22 positioned approximately 90° apart about the periphery of body 16, staggered in a fore-to-aft manner between adjacent ears 22. However, other configurations are also possible.

Figure 1:
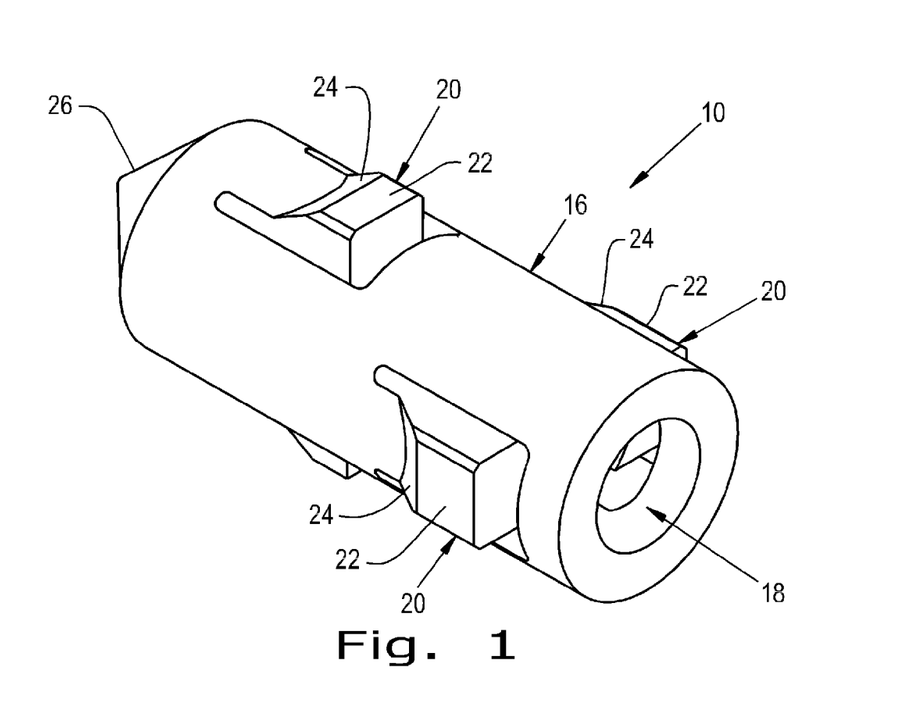
FIG. 1 is a perspective view of an embodiment of an anchor forming part of a bone fusion device of the present invention.
Figure 2:
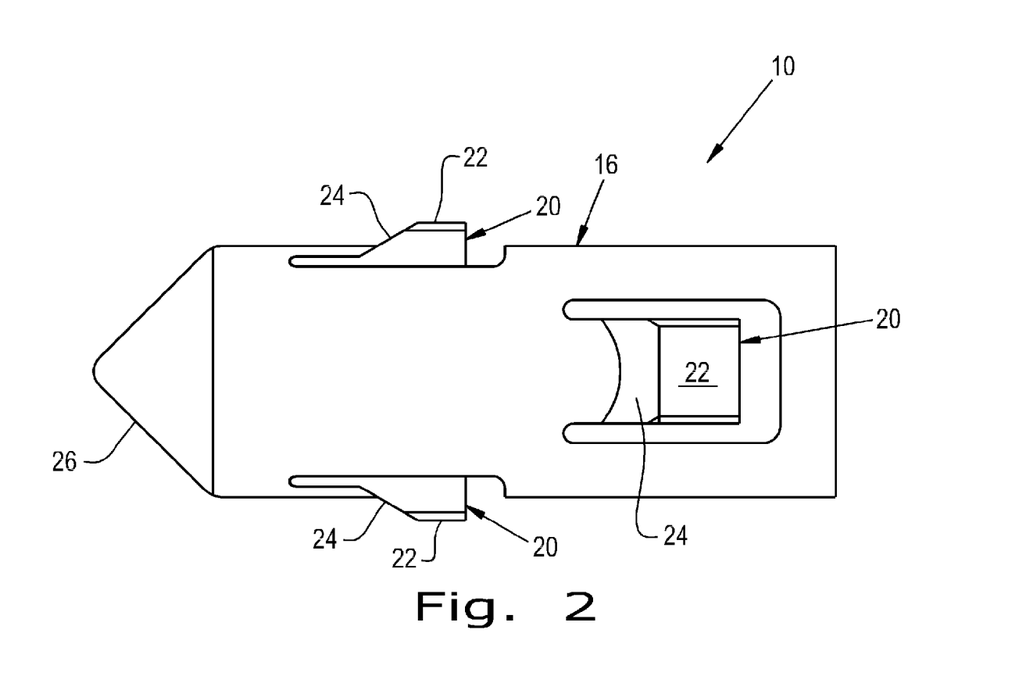
FIG. 2 is a side view of the anchor shown in FIG. 1.
Figure 3:
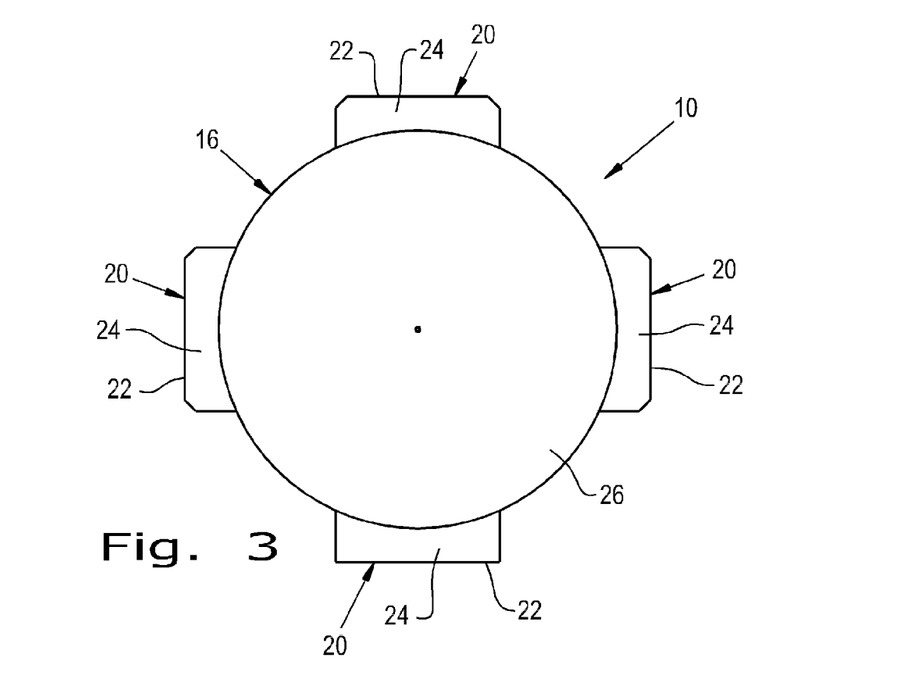
FIG. 3 is an end view of the anchor shown in FIGS. 1 and 2.
Figure 4:
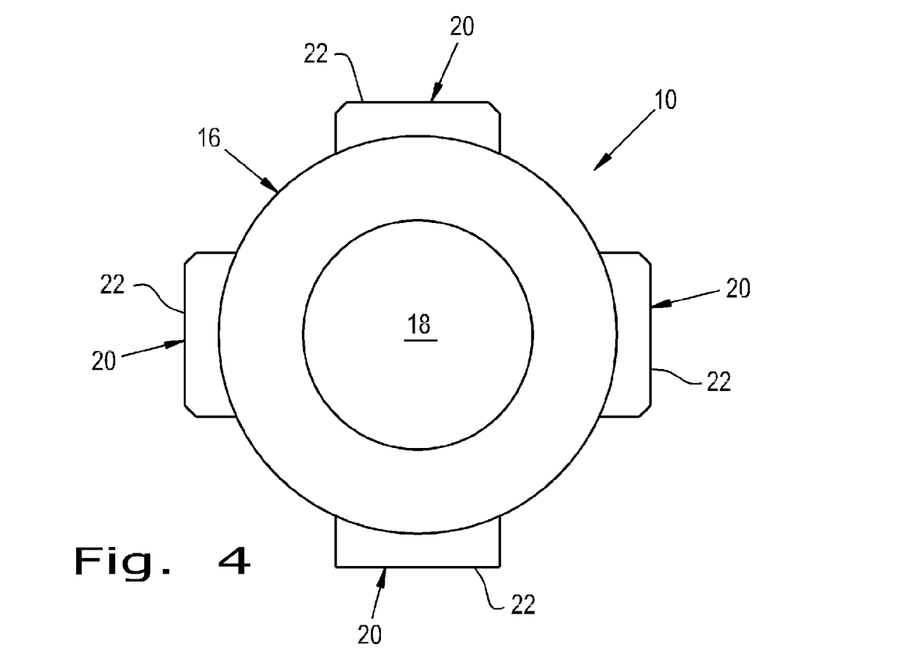
FIG. 4 is an opposite end view of the anchor shown in FIG. 3.
Figure 5:
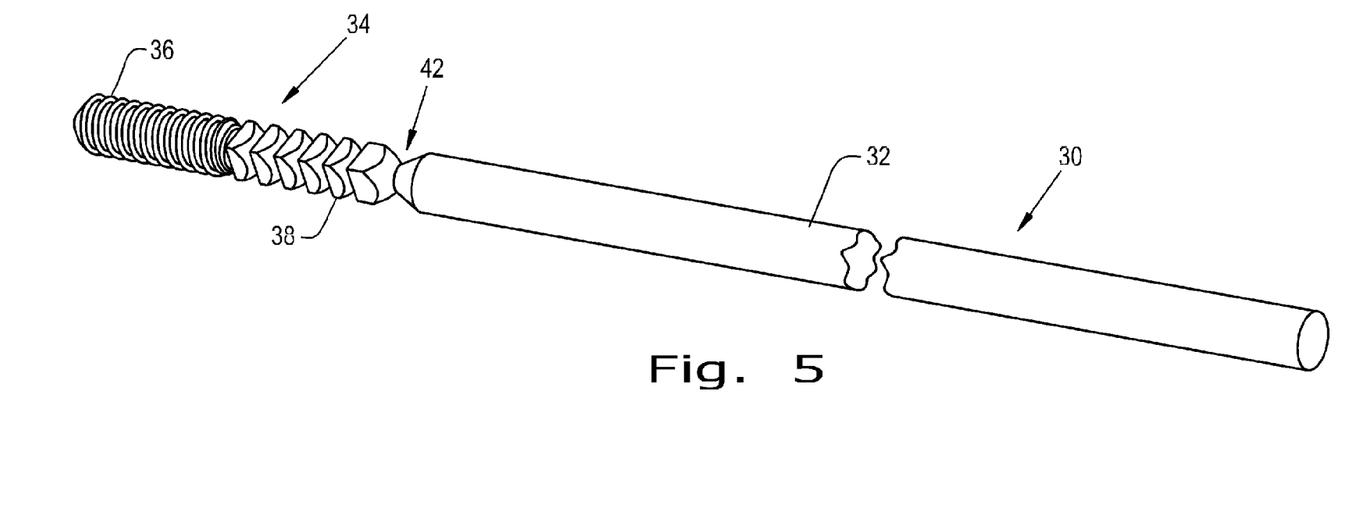
FIG. 5 is a perspective view of an embodiment of a rod used with the anchor shown in FIGS. 1-4.
Figure 6:
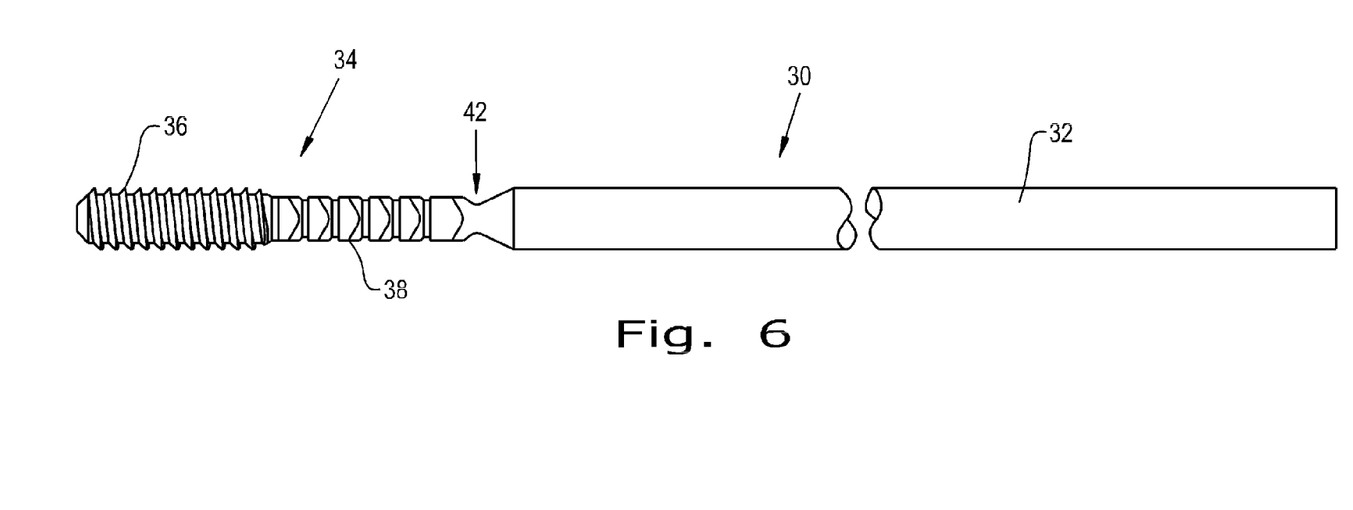
FIG. 6 is a side view of the rod shown in FIG. 5.
Figure 7:
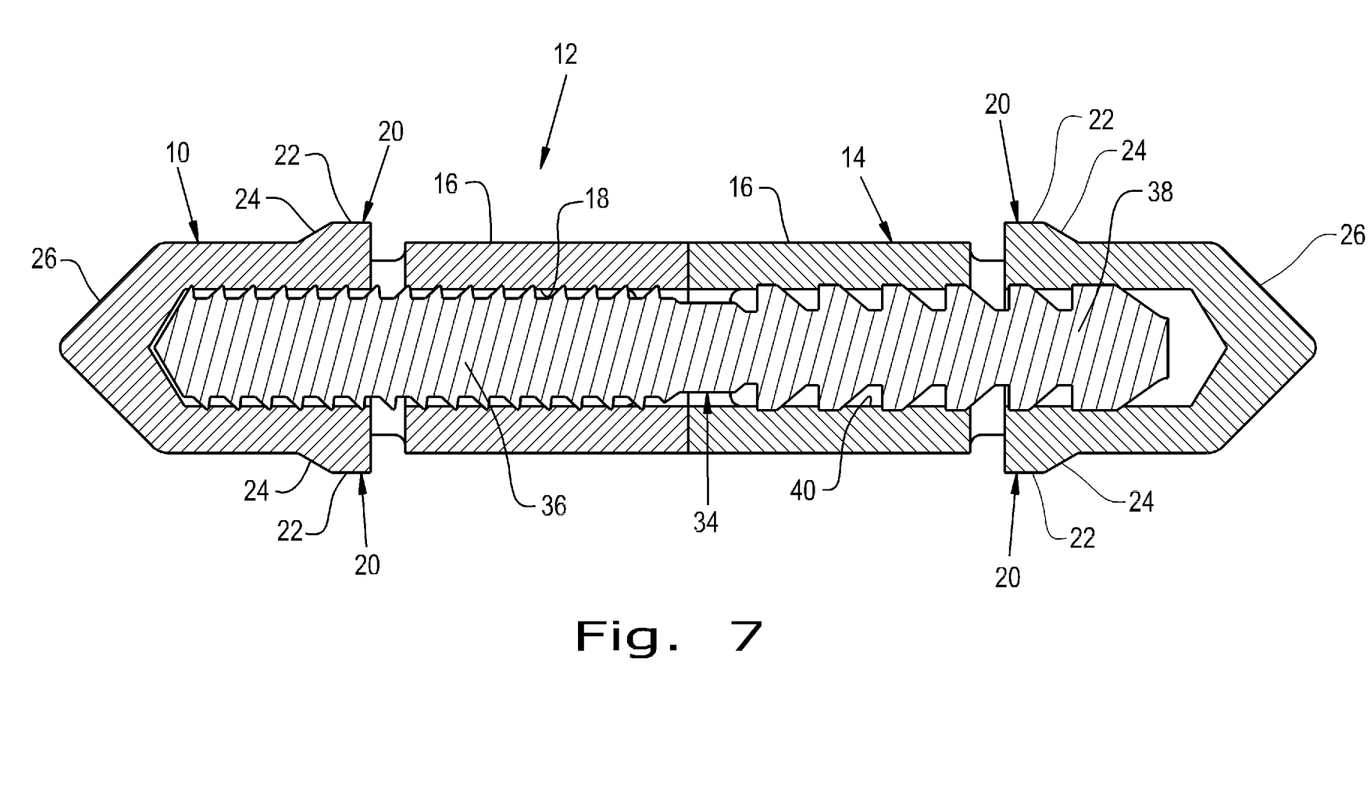
FIG. 7 is a side sectional view of the anchor shown in FIGS. 1-4, with the distal end of the rod threaded therein.

Referring now to FIGS. 5 and 6, there is shown an embodiment of a rod 30 which forms a part of the bone fusion device 12 of the present invention. Rod 30 generally includes a handle 32 and a distal end 34. Distal end 34 defines a pin which is associated with each of first anchor 10 and second anchor 14 (FIG. 7). More particularly, the pin defined by distal end 34 includes a first end 36 which is insertable into the first axial bore 18 of first anchor 10, and a second end 38 which is insertable into a second axial bore 40 of second anchor 14.

Rod 30 also includes a breakaway portion 42 positioned between handle 32 and distal end/pin 34. Breakaway portion 42 allows handle 32 to be manually separated from distal end/pin 34. As may be seen in each of FIGS. 5 and 6, breakaway portion 42 has a cross-section which is reduced in thickness relative to handle 32. In the illustrated embodiment, breakaway portion 42 has a cross section which is substantially circular, but may be differently shaped depending upon the application. For example, breakaway portion 42 can have a cross-section which is hexagonal, elliptical, triangular, etc.

Referring now to FIG. 7, bone fusion device 12 is shown in an assembled state. When in an assembled state, first end 36 of pin 34 is threaded into first anchor 10, and second end 38 of pin 34 is press-fitted into and snap-locked within second anchor 14. When pin 34 is installed within each anchor 10 and 14, tabs 20 are biased radially outward such that ears 22 dig into the sidewall of the hole formed in the bone, thereby preventing rotation of anchors 10 and 14 within the holes. First anchor 10 and second anchor 14 preferably abut each other in an end-to-end manner, thereby providing sufficient rigidity for fusion of the adjacent phalanges.

In another embodiment (not shown) similar to FIG. 7, first anchor 10 can be eliminated and first end 36 can be screwed directly into a hole formed in a bone. Second end 38 can still be press-fitted into the second axial bore 40 formed in second anchor 14. The orientation of first end 36 installed in one bone and second anchor 14 installed in an adjacent bone can be either direction, proximal or distal.

Figure 8:
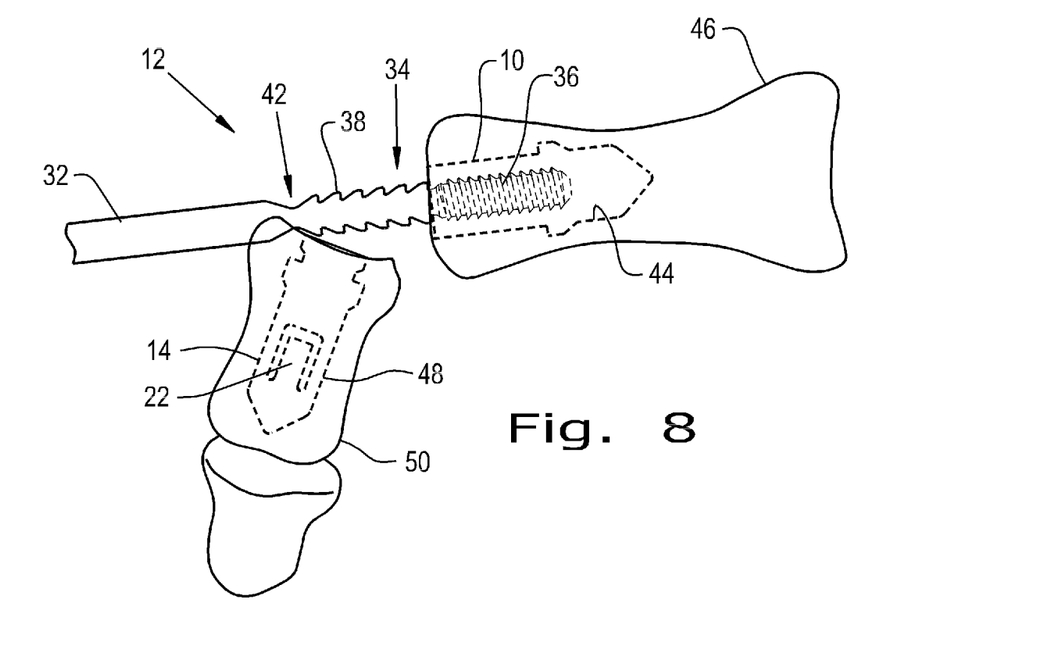
FIG. 8 is a side view of a pair of anchors inserted within adjacent ends of phalanges, with the distal end of the rod inserted into one of the anchors, prior to detachment of the handle from the distal end of the rod.
Figure 9:
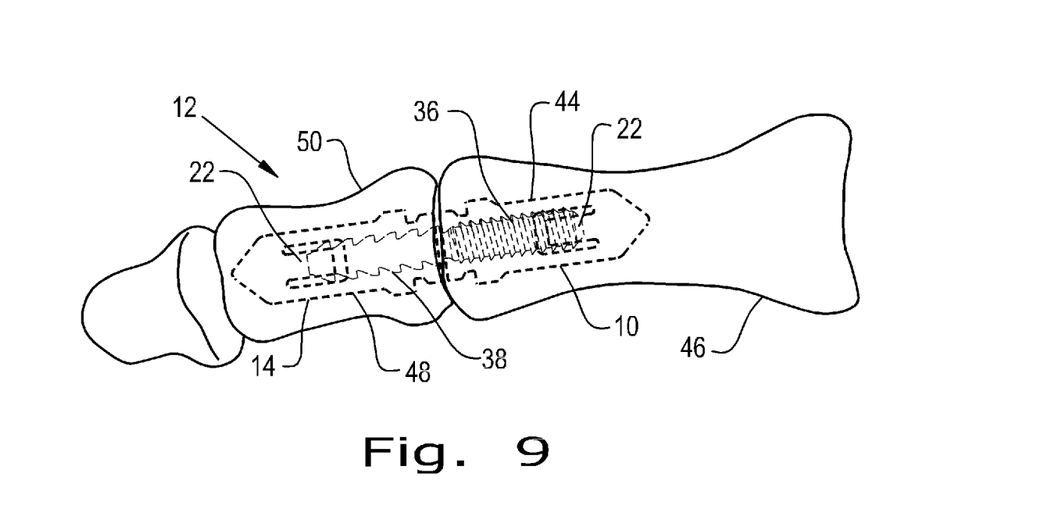
FIG. 9 is a side view of the anchor shown in FIG. 8, with the pin formed by the distal end of the rod inserted within each of the anchors.
Figure 10:
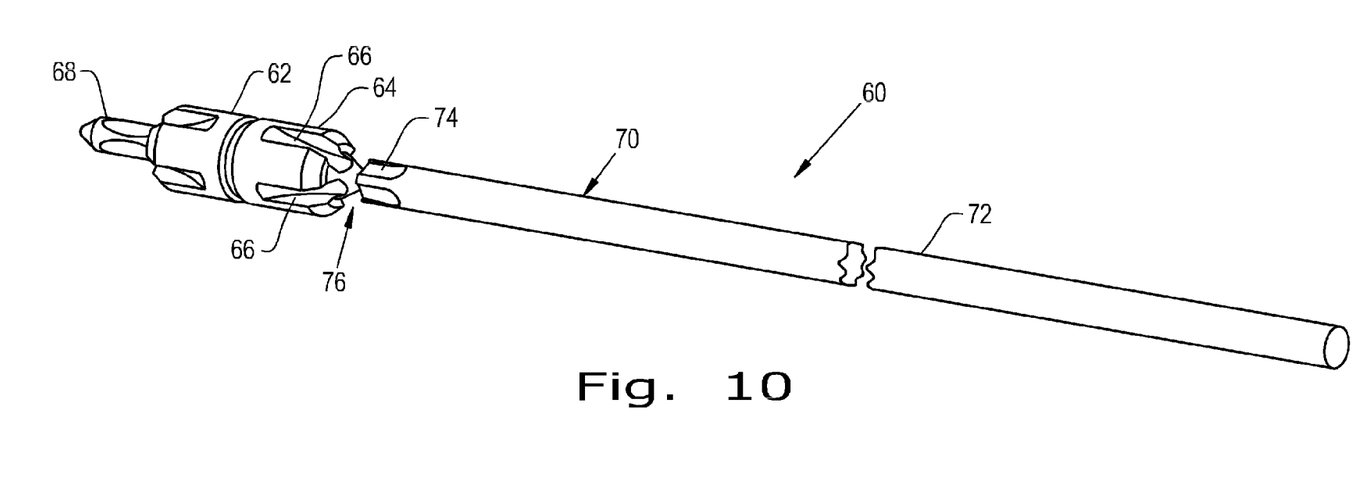
FIG. 10 is a perspective view of another embodiment of a bone fusion device of the present invention.
Figure 11:
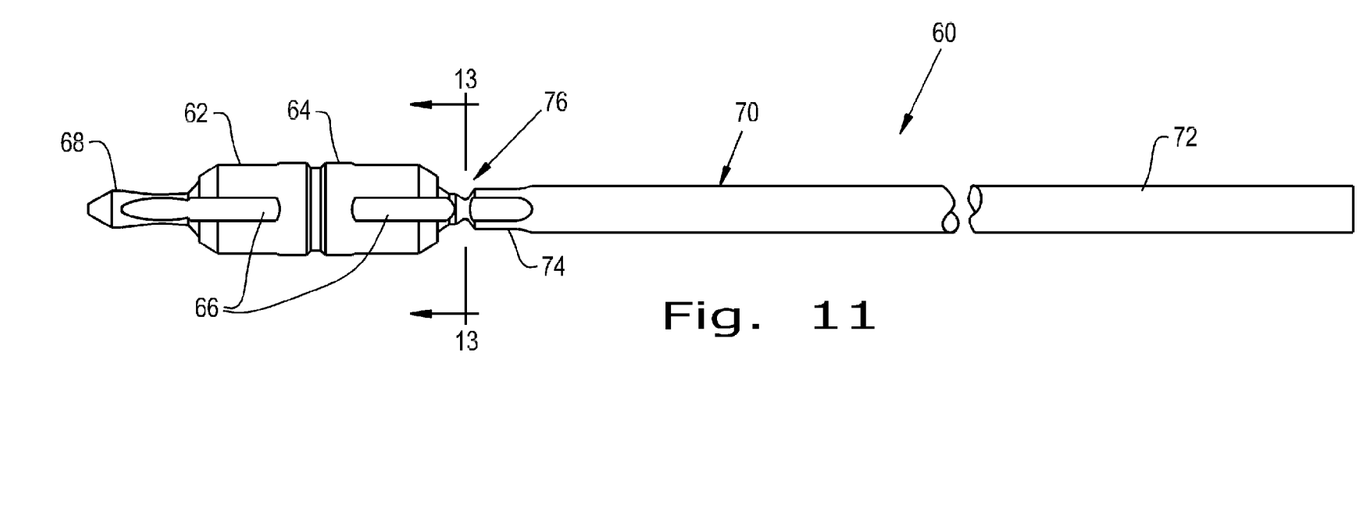
FIG. 11 is a side view of the bone fusion device shown in FIG. 10.
Figure 12:
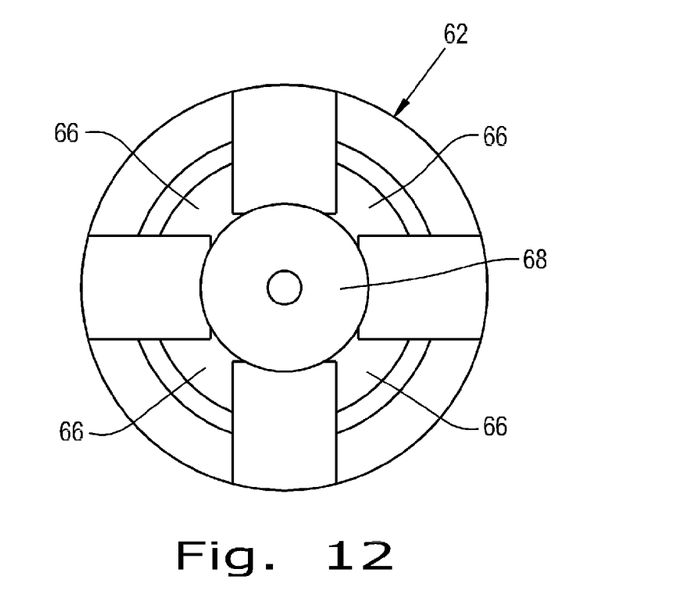
FIG. 12 is a distal end view of the bone fusion device shown in FIGS. 10 and 11.
Figure 13:
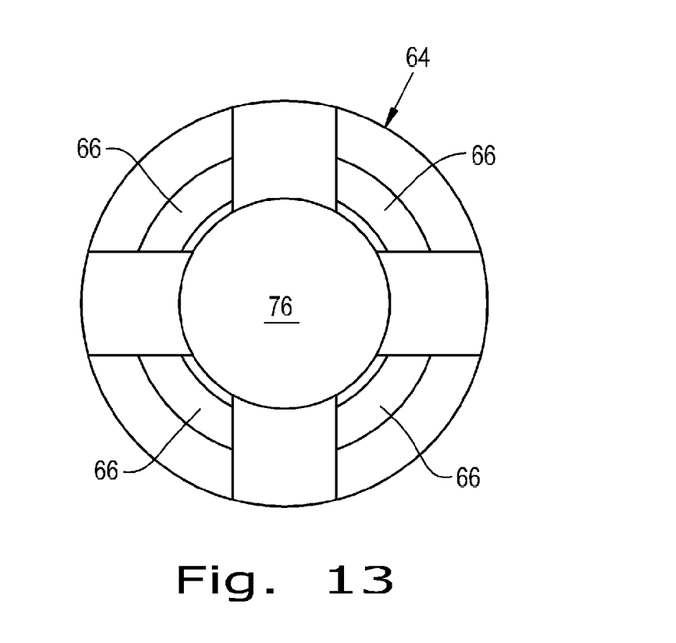
FIG. 13 is a proximal end view of the bone fusion device shown in FIGS. 10-12, taken along line 13-13 in FIG. 11.

FIGS. 8 and 9 illustrate a surgical procedure utilizing bone fusion device 12. A hole 44 is formed in the distal end of a proximal phalange 46 by drilling or other means. First anchor 10 has a diameter which is slightly larger than the inside diameter of hole 44 so as to form an interference fit therewith. First anchor 10 is inserted into the hole 44 using any suitable placement technique, such as manually or with a tool. The first end 36 of distal end/pin 34 is then threaded into first anchor 10 until seated adjacent closed end 26. This may be accomplished by either manually grasping handle 32, or attaching handle 32 to a tool or driver. When first end 38 of distal end/pin 34 is in place within first axial bore 18, the tabs 20 prevent rotation of first anchor 10 within hole 44.

With another option, first anchor 10 which is shown in phantom lines in FIGS. 8 and 9 can be eliminated, and first end 36 can be screwed directly into a hole formed in the proximal phalange 46. The inside diameter of the hole formed in the proximal phalange 46 would be sized to allow the external threads of first end 36 to self-tap into the hole.

Rod 30 is then manually bent and/or twisted to separate handle 32 from distal end/pin 34 at breakaway portion 42. After separation of handle 32 from distal end 34, distal end 34 then becomes the pin 34 that is received within each axial bore of first anchor 10 and second anchor 14. A hole 48 is also formed in the proximal end of distal phalange 50. Second anchor 14 is inserted into the hole 48 using any suitable placement technique, as noted above. The formation of hole 48 within distal phalange 50 and placement of second anchor 14 within hole 48 can occur either before or after placement of distal end/pin 34 within first anchor 10, depending upon the preferences of the surgeon. Distal phalange 50 is distended a sufficient amount allowing second anchor 14 to be positioned longitudinally adjacent to second end 40 of pin 34. Second anchor 14 is slid over second end 40 of pin 34 until second anchor 40 is seated against first anchor 10 (snap fit). With bone fusion device 12 in an assembled state as shown in FIG. 9, fusion between proximal phalange 46 and distal phalange 50 can occur. Alternatively, the orientation of first anchor 10 and second anchor 14 can be reversed, such that second anchor 14 is located in the proximal phalange and first anchor 10 is located in the distal phalange.

Referring now to FIGS. 10-13, there is shown another embodiment of a bone fusion device 60 of the present invention. Bone fusion device 60 is similar to bone fusion device 12, in that it includes a first anchor 62 and a second anchor 64 which are received within respective holes formed in adjacent bones. However, bone fusion device 12 differs from bone fusion device 60 in that first anchor 62 and second anchor 64 are monolithically formed together as a single piece. First anchor 62 and second anchor 64 each include a plurality of anti-rotation features which inhibit rotational movement relative to a respective phalange when placed within a respective hole of the phalange. In the embodiment shown in FIGS. 10-13, each anchor 62 and 64 includes four notches 66 which are formed in an exterior surface thereof at approximate 90° angular intervals. Notches 66 dig into the bone to prevent rotation when anchors 62 and 64 are placed within the respective holes.

First anchor 62 includes a tip 68 which extends axially in a direction opposite from rod 70. Tip 68 preferably has an outside diameter which is slightly larger than a K-wire used to form an initial hole in the end of a phalange, and thereby forms an interference fit with the hole formed by the K-wire.

Rod 70 has a handle 72 with a distal end 74 which is attached to a proximal end of second anchor 64. A breakaway portion 76 located at the distal end 74 allows handle 72 to be manually separated from second anchor 64. Breakaway portion 76 has a circular cross section in the embodiment shown in FIGS. 10-13 (see FIG. 13), but can have a different shaped cross-section for other applications.

Figure 14:
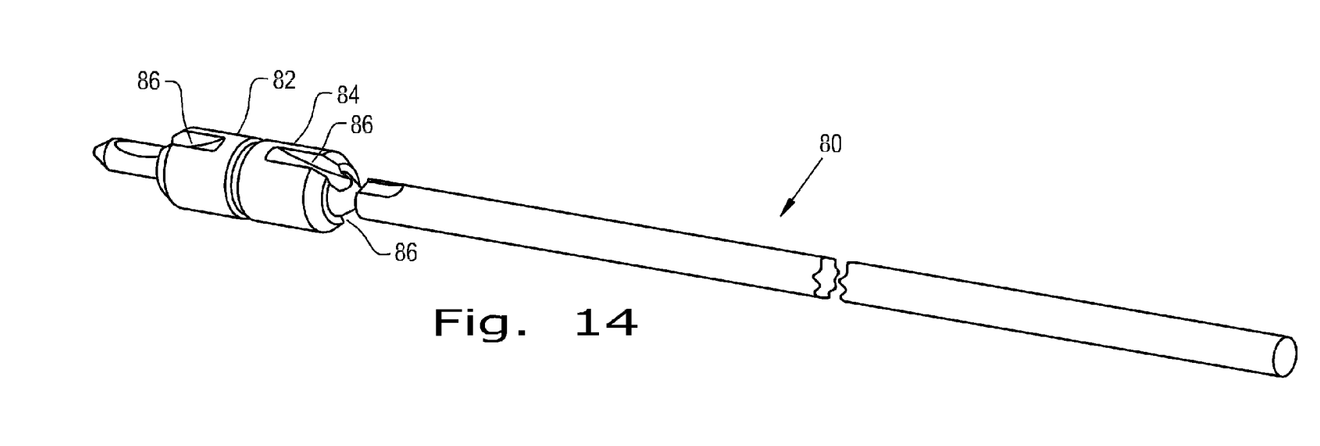
FIG. 14 is a perspective view of yet another embodiment of a bone fusion device of the present invention.
Figure 15:
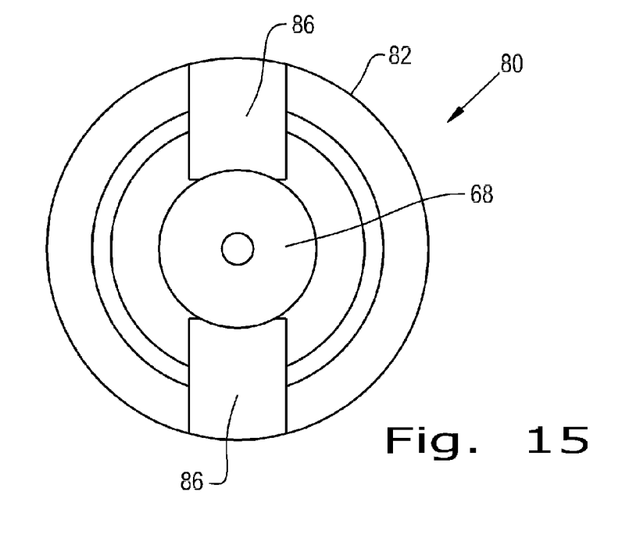
FIG. 15 is a distal end view of the bone fusion device shown in FIG. 14.

Referring now to FIGS. 14-15, there is shown yet another embodiment of a bone fusion device 80 of the present invention. Bone fusion device 80 is similar to bone fusion device 60 shown in FIGS. 10-13. However, bone fusion device 80 differs from bone fusion device 60 in that first anchor 82 and second anchor 84 each include only two notches 86 which are formed in an exterior surface thereof at approximate 180° angular intervals.

Figure 16:
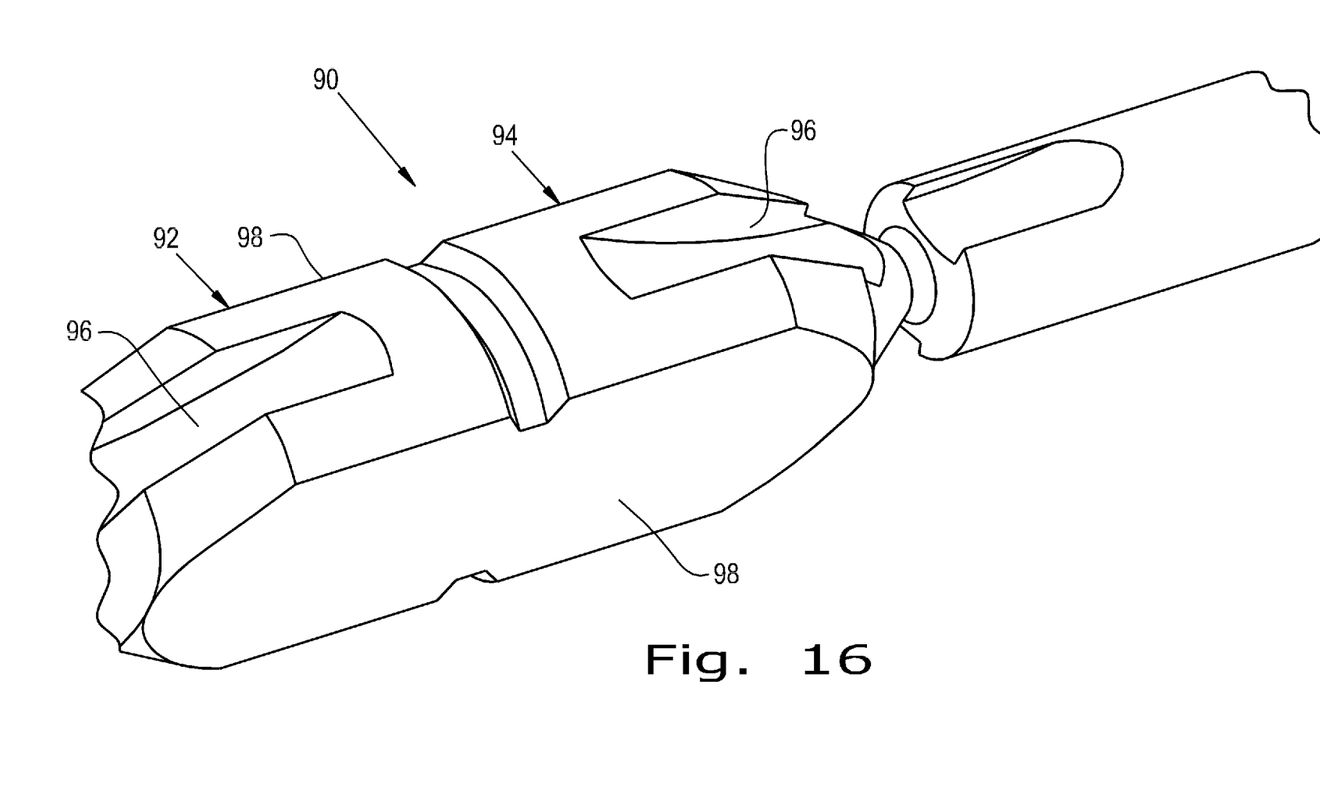
FIG. 16 is a fragmentary, perspective view of still another embodiment of a bone fusion device of the present invention.

Referring now to FIG. 16, there is shown yet another embodiment of a bone fusion device 90 of the present invention. Bone fusion device 90 is similar to bone fusion device 80 shown in FIGS. 14-15, in that first anchor 92 and second anchor 94 each include two notches 96 which are formed in an exterior surface thereof at approximate 180° angular intervals. However, the integral first anchor 92 and second anchor 94 each have an exterior surface with a pair of parallel, generally planar walls 98 which further assist in preventing rotation of first anchor 92 and second anchor 94 when installed within respective holes in adjacent bones.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A bone fusion device, comprising:
a first anchor for insertion into a first hole formed in a first phalange;
a second anchor for insertion into a second hole formed in a second phalange; and
a rod including a handle and a distal end, said rod including a breakaway portion between said handle and said distal end allowing said handle to be manually separated from said distal end, said distal end adapted to couple the first anchor and the second anchor rigidly to one another to enable fusion of the first phalange to the second phalange after the handle has been manually separated from the distal end at the breakaway portion.

2. The bone fusion device of claim 1, wherein said breakaway portion has a reduced cross section relative to the handle.

3. The bone fusion device of claim 2, wherein said reduced cross section is substantially circular.

4. The bone fusion device of claim 2, wherein said handle may be manually separated from said distal end by at least one of manually bending and twisting said handle and breaking said rod at said breakaway portion.

5. The bone fusion device of claim 1, wherein said first anchor and said second anchor are discrete parts, said first anchor including a first axial bore and said second anchor including a second axial bore, and wherein said distal end of said rod defines a pin including a first end insertable into said first axial bore and a second end insertable into said second axial bore.

6. The bone fusion device of claim 5, wherein at least one of said first anchor and said second anchor includes at least one anti-rotation feature to inhibit rotational movement relative to a respective phalange when placed within a respective hole of the phalange.

7. The bone fusion device of claim 6, wherein each said anti-rotation feature includes at least one radially movable tab, each said tab being biased radially outward upon insertion of said pin into said respective first axial bore and said second axial bore.

8. The bone fusion device of claim 5, wherein said first end is insertable into said first axial bore when said breakaway portion is intact, and wherein said second end is insertable into said second axial bore after said breakaway portion is detached.

9. The bone fusion device of claim 8, wherein said first end has an external threaded surface for mating with said first axial bore, and said second end is pressed into said second axial bore.

10. The bone fusion device of claim 9, wherein said second end includes an anti-rotation feature to inhibit rotational movement of said pin relative to said second anchor.

11. The bone fusion device of claim 10, wherein said second end has a non-circular cross section defining said anti-rotation feature.

12. The bone fusion device of claim 5, wherein at least one of said first end and said second end includes an anti-rotation feature to inhibit rotational movement of said pin.

13. A bone fusion device, comprising:
a first anchor for insertion into a first hole formed in a first portion of bone;
a second anchor for insertion into a second hole formed in a second portion of bone, wherein the first portion of bone is disconnected from the second portion of bone; and
a rod including a handle and a distal end, said rod including a breakaway portion between said handle and said distal end allowing said handle to be manually separated from said distal end, said distal end including a in structure adapted to rigidly couple the first anchor adjacent to the second anchor on the in structure to enable fusion of the first portion of bone with the second portion of bone after the handle has been manually separated from the distal end at the breakaway portion.

14. The bone fusion device of claim 13, wherein said breakaway portion has a reduced cross section relative to the handle.

15. The bone fusion device of claim 13, wherein said handle may be manually separated from said distal end by at least one of manually bending and twisting said handle and breaking said rod at said breakaway portion.

16. The bone fusion device of claim 13, wherein the first anchor includes an axial bore, and said distal end of said rod is insertable into said axial bore.

17. The bone fusion device of claim 16, wherein said first anchor includes at least one anti-rotation feature to inhibit rotational movement relative to the bone.

18. The bone fusion device of claim 17, wherein each said anti-rotation feature includes a radially movable tab which is biased radially outward upon insertion of said distal end of said rod into said axial bore.

19. The bone fusion device of claim 13, wherein said pin structure includes an externally threaded first end for threaded engagement with an axial bore in the first anchor, and a second end for insertion into a second axial bore within the second anchor after the handle is broken off at the breakaway portion.

* * * * *

UNITED STATES PATENT AND TRADEMARK OFFICE
CERTIFICATE OF CORRECTION

PATENT NO. : 9,517,098 B2  
APPLICATION NO. : 13/935107  
DATED : December 13, 2016  
INVENTOR(S) : David Anderson Page 1 of 1

It is certified that error appears in the above-identified patent and that said Letters Patent is hereby corrected as shown below:

In the Claims

In Column 6, Line 59, in Claim 13, delete "in" and insert --pin--, therefor

In Column 6, Line 60, in Claim 13, delete "in" and insert --pin--, therefor

Signed and Sealed this  
Nineteenth Day of June, 2018

Andrei Iancu  
*Director of the United States Patent and Trademark Office*